United States Patent
Paulos

(10) Patent No.: US 9,320,634 B2
(45) Date of Patent: Apr. 26, 2016

(54) TRAINING BRACE ASSEMBLY AND METHODS OF USE

(75) Inventor: Lonnie Paulos, Pensacola Beach, FL (US)

(73) Assignee: The Lonnie and Shannon Paulos Trust (as Amended and Restated) F/K/A The James Dizikis Trust Dated February 26, 2008, Salt Lake City, UT (US)

( * ) Notice: Subject to any disclaimer, the term of this patent is extended or adjusted under 35 U.S.C. 154(b) by 724 days.

(21) Appl. No.: 13/541,796

(22) Filed: Jul. 5, 2012

(65) Prior Publication Data

US 2012/0270708 A1 Oct. 25, 2012

Related U.S. Application Data

(63) Continuation-in-part of application No. 13/188,506, filed on Jul. 22, 2011, now Pat. No. 8,808,211, which is a continuation-in-part of application No. PCT/US2009/067152, filed on Dec. 8, 2009, and a (Continued)

(51) Int. Cl.
*A61F 5/01* (2006.01)

(52) U.S. Cl.
CPC ....... *A61F 5/0102* (2013.01); *A61F 2005/0179* (2013.01)

(58) Field of Classification Search
USPC ............. 602/5, 16, 20, 23, 26–27, 61, 64–65; 128/882, 892–893, 875–876; 2/228, 69
See application file for complete search history.

(56) References Cited

U.S. PATENT DOCUMENTS

| | | | |
|---|---|---|---|
| 2,603,786 | A | 7/1953 | Haines |
| 4,240,414 | A | 12/1980 | Theisler |
| 4,294,238 | A | 10/1981 | Woodford |
| 4,556,054 | A | 12/1985 | Paulseth |
| 4,702,234 | A | 10/1987 | Hutjens et al. |
| 4,817,588 | A | 4/1989 | Bledsoe |
| 4,854,308 | A | 8/1989 | Drillio |
| 5,063,916 | A | 11/1991 | France et al. |
| 5,399,153 | A | 3/1995 | Caprio, Jr. et al. |

(Continued)

FOREIGN PATENT DOCUMENTS

| | | |
|---|---|---|
| EP | 1462072 | 9/2004 |
| JP | 01-150916 | 10/1989 |

(Continued)

OTHER PUBLICATIONS

Hawthorne, Ophelia Althea, USPTO, U.S. Appl. No. 13/188,506, Notice of Allowance, mailed Apr. 11, 2014, 14 pages, US.

(Continued)

*Primary Examiner* — Ophelia A Hawthorne
(74) *Attorney, Agent, or Firm* — John J Brooks, III; John Brooks Law LLC

(57) ABSTRACT

Embodiments of the training brace assembly utilize an elastic training portion about a body portion to provide a resistance force to the limbs about the body portions. The elastic training portion may be positioned from attachment points on upper and lower mounting portions to provide the resistance force that influences the movement of the mounting portions and the body portion. In embodiments for a hip joint as the body portion, the training brace assembly provides a progressive resistance force that may assist in neuromuscular training of the hip joint.

18 Claims, 10 Drawing Sheets

Related U.S. Application Data continuation-in-part of application No. PCT/US2009/046183, filed on Jun. 3, 2009, application No. 13/541,796, filed on Jul. 5, 2012, which is a continuation-in-part of application No. 12/993,258, filed as application No. PCT/US2009/046183 on Jun. 3, 2009, now Pat. No. 8,852,133.

(60) Provisional application No. 61/504,341, filed on Jul. 5, 2011, provisional application No. 61/466,909, filed on Mar. 23, 2011, provisional application No. 61/262,723, filed on Nov. 19, 2009, provisional application No. 61/263,737, filed on Nov. 23, 2009, provisional application No. 61/058,555, filed on Jun. 3, 2008, provisional application No. 61/148,973, filed on Feb. 1, 2009.

(56) References Cited

U.S. PATENT DOCUMENTS

| | | | |
|---|---|---|---|
| 5,417,647 | A | 5/1995 | Down |
| 5,512,039 | A | 4/1996 | White |
| 5,891,079 | A | 4/1999 | Barnes |
| 6,368,297 | B1 | 4/2002 | Smits |
| 7,198,610 | B2 | 4/2007 | Ingimundarson et al. |
| 7,959,591 | B2 * | 6/2011 | Powers et al. .......... 602/62 |
| 8,007,457 | B2 | 8/2011 | Taylor et al. |
| 8,167,829 | B2 | 5/2012 | Sterling et al. |
| 2002/0010410 | A1 | 1/2002 | Steponovich |
| 2003/0204156 | A1 | 10/2003 | Nelson et al. |
| 2003/0232701 | A1 | 12/2003 | Latella, Jr. |
| 2006/0000478 | A1 * | 1/2006 | Taylor .......... 128/869 |
| 2006/0089583 | A1 | 4/2006 | Reinhardt |
| 2008/0083055 | A1 | 4/2008 | Onda et al. |
| 2009/0090027 | A1 | 4/2009 | Baudouin et al. |
| 2010/0069802 | A1 * | 3/2010 | Motyer .......... 602/4 |
| 2010/0088803 | A1 | 4/2010 | Orloff et al. |
| 2011/0009793 | A1 | 1/2011 | Lucero et al. |

FOREIGN PATENT DOCUMENTS

| | | |
|---|---|---|
| JP | 01150916 | 10/1989 |
| KR | 10-0742181 | 7/2007 |
| KR | 100742181 | 7/2007 |
| WO | WO9400082 | 1/1994 |
| WO | 2007020372 A2 | 2/2007 |

OTHER PUBLICATIONS

Lewis, Kim M., USPTO, U.S. Appl. No. 12/993,258, Notice of Allowance mailed Jun. 4, 2014, 26 pages, US.

Christopher Geiser, Kristian M. O'Connor, Jennifer E. Earl, Effects of Isolated Hip Abductor Fatigue on Frontal Plane Knee Mechanics, Marquette University e-Publications@Marquette, Health Sciences Faculty Research and Publications, College of Health Sciences, Medicine and Science in Sports and Exercise, vol. 42, No. 3, Mar. 2010, pp. 535-545.

Sue D. Barber-Westin, Stephaine T. Smith, Thomas Campbell, and Frank R. Noyes, The Drop-Jump Video ScreeningTest: Retention of Improvement in Neuromuscular Control in Female Volleyball Players, Journal of Strength and Conditioning Research 2010 National Strength and Conditioning Association, vol. 0, No. 0, Month 2010.

Cale A. Jacobs, Timothy L. Uhl, Carl G. Mattacola, Robet Shapiro, William S. Rayens, Hip Abductor Function and Lower Extremity Landing Kinematics: Sex Differences, Journal of Athletic Training 2007; 42(1):76-83 by the National Athletic Trainers' Association, Inc. www.journalofathletictraining.org.

Gregory D. Myer, Kevin R. Ford, Joseph P. Palumbo, and Timothy E. Hewett, Neuromuscular Training Improves Performance and Lower-Extremity Biomechanics in Female Athletes, Journal of Strength and Conditioning Research, 2005, 19(1), 51-60, 2005 National Strength & Conditioning Association.

WIPO International Searching Authority, International Search Report and the Written Opinion of the International Searching Authority of PCT Application No. PCT/US2009/67152 to Lonnie E. Paulos.

USPTO, Hawthorne, Ophelia Althea, USPTO Office Action for pending U.S. Appl. No. 13/188,506, 17 pages, mailed Sep. 3, 2013, USA.

USPTO, Hawthorne, Ophelia Althea, USPTO Office Action for U.S. Appl. No. 13/188,506, 17 pages, mailed Aug. 5, 2013, USA.

USPTO, Lewis, Kim M, USPTO Office Action for U.S. Appl. No. 12/993,258, 14 pages, mailed Aug. 19, 2013, USA.

WIPO, Moon Song, John, International Search Report and the Written Opinion of the International Searching Authority, Korean Intellectual Property Office for PCT Application No. PCT/US2009/046183 to Lonnie E. Paulos, 11 pages, mailed Jan. 18, 2010, Korea.

U.S. Appl. No. 13/188,506, Final Office Action dated Jan. 15, 2014, 11 pages.

U.S. Appl. No. 12/993,258, Final Office Action dated Feb. 4, 2014, 13 pages.

* cited by examiner

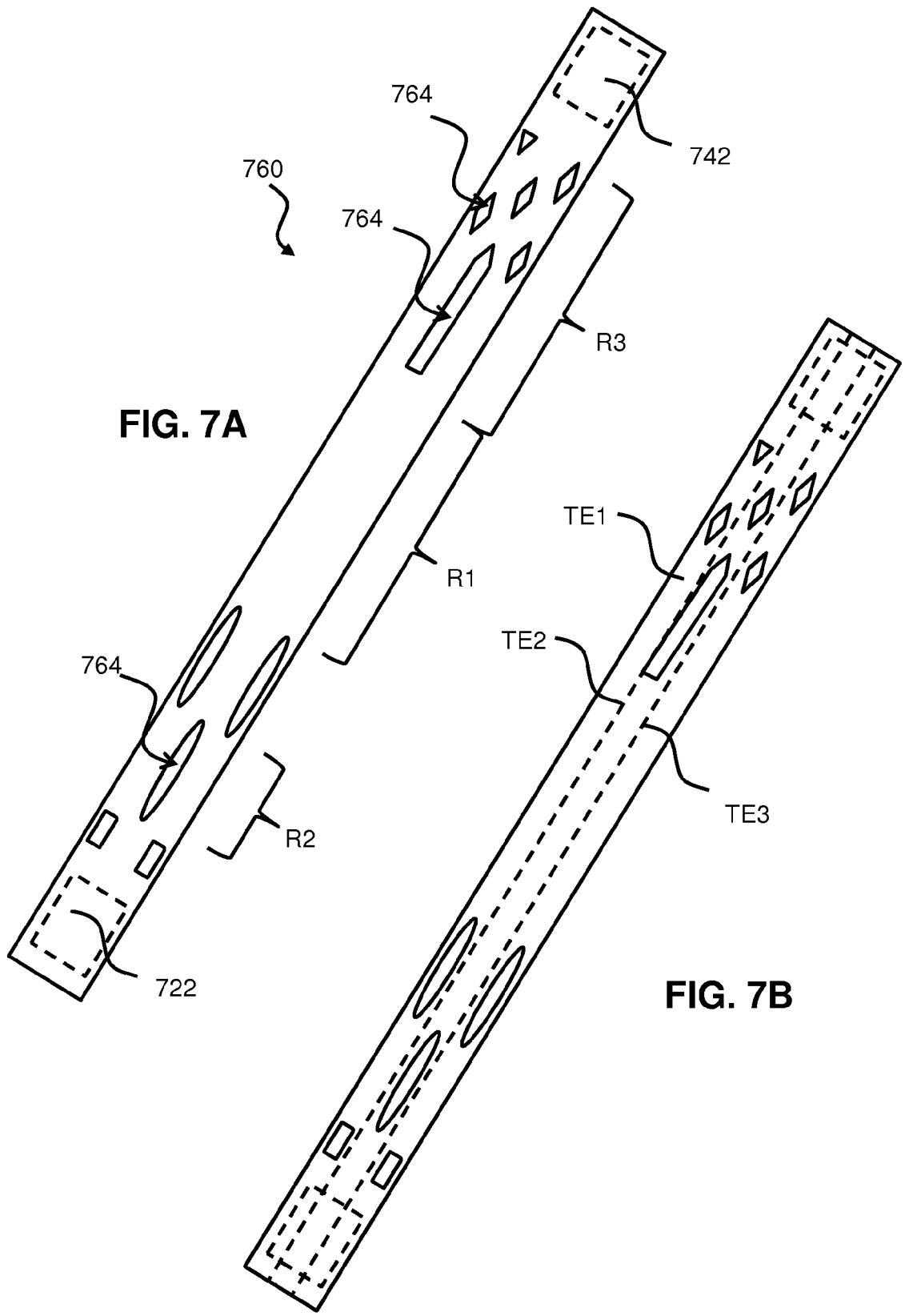

TRAINING BRACE ASSEMBLY AND METHODS OF USE

CROSS-REFERENCE TO RELATED APPLICATIONS

The present application is a Continuation in Part Application of U.S. patent application Ser. No. 13/188,506 filed Jul. 22, 2011 which is a Continuation in Part Application of PCT Application No. PCT/US09/67152, filed Dec. 8, 2009 which also claims benefit of U.S. Provisional Application Ser. No. 61/466,909, filed Mar. 23, 2011, PCT Application No. PCT/US09/67152 claims benefit of U.S. Provisional Application Ser. No. 61/262,723, filed Nov. 19, 2009, PCT Application No. PCT/US09/67152 also claims benefit of U.S. Provisional Application Ser. No. 61/263,737, filed Nov. 23, 2009, PCT Application No. PCT/US09/67152 is also a Continuation in Part Application of PCT Application No. PCT/US09/46183, filed Jun. 3, 2009, PCT Application No. PCT/US09/46183 claims benefit of U.S. Provisional Application Ser. No. 61/058,555, filed Jun. 3, 2008, and PCT Application No. PCT/US09/46183 claims benefit of U.S. Provisional Application Ser. No. 61/148,973, filed Feb. 1, 2009; the present application is also a Continuation in Part Application of U.S. patent application Ser. No. 12/993,258, filed Nov. 18, 2010, which is the U.S. National Stage application of International Application No. PCT/US09/46183, filed Jun. 3, 2009, PCT Application No. PCT/US09/46183 claims benefit of U.S. Provisional Application Ser. No. 61/058,555, filed Jun. 3, 2008, and PCT Application No. PCT/US09/46183 claims benefit of U.S. Provisional Application Ser. No. 61/148,973, filed Feb. 1, 2009; the present application also claims benefit of U.S. Pat. Application No. 61/504,341 filed Jul. 5, 2011; and the entire contents of all the above referenced applications are herein incorporated by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The present invention relates to braces that can help train proper movement of a limb, and more specifically relates to training brace configurations and methods utilizing an elastic training portion that assists in proprioceptive/neuromuscular-training a limb about a joint.

Braces have been used to reduce the incidence of joint injury and to help recuperation after injury.

Neuromuscular training is also starting to be used to reduce injury and aid in recuperation after injury. Using the knee as an example, anterior cruciate ligament (ACL) injuries and patellofemoral pain syndrome (PFPS) are common injuries to the knee that have been associated with hip weakness. Some studies have linked the risk of experiencing either injury to alterations in the frontal plane knee angle and moment during activity. Further studies have shown that limb alignment can be improved by neuromuscular retraining encouraging neutral alignment of hips, knees and ankles of athletes.

One component of neuromuscular training includes proprioception. Proprioception involves nerve endings and receptors throughout the body that feed the central nervous system with information which in turn communicate to the rest of the body how to react to that situation such as what amount of tension to be applied to a muscle around a joint. These receptors are located in ligaments, skin, muscles, joint capsules, and tendons. Together with information from the eyes and the ears, this information assists in hand, foot and eye coordination, and also balance. By repeated use of these nerves and receptors through certain movements patterns, the nervous system become more efficient in communicating and coordinating this information throughout the body.

Injuries or surgery can also alter proprioception. For example, an injury or just not using our bodies for a period of time can create less stimulation to the proprioceptors. Pain inhibits proprioception and can alter muscle activation patterns such that the body can lose some of its proprioceptive ability. Loss of proprioception can cause a delay in the nervous system processing information which can effect muscular activation patterns as well as delay the body's attempt to protect the area.

Neuromuscular and proprioception training has been shown to be effective in reducing the incidence of certain types of sports injuries among adolescent and young adult athletes during pivoting sports. The benefit of proprioception may even be greater for those with a history of sports injury.

SUMMARY OF THE INVENTION

The following summary is included only to introduce some concepts discussed in the Detailed Description below. This summary is not comprehensive and is not intended to delineate the scope of protectable subject matter.

Some embodiments of the training brace assembly utilize an elastic training strap, as the elastic portion of the training brace, attached to mounting facilities about a joint to influence, or "train" the movement of limbs about the joint. The elastic portion of the training brace has elastic properties that allow it to provide progressive resistance as the strap is stretched by the limb movement. The positioning of the elastic training strap portion can be made such that the resistance can be varied to provide one level of resistance in one portion of joint movement and another level of resistance in another portion of movement. Additionally, the elastic training strap can be positioned or wrapped around the body so that the resistance can create forces that urge one mounting facility, and the body portion it is engaged with, to move in one or more directions, such as to rotate, relative to the other mounting facility.

One example embodiment of a training brace assembly for a body portion comprises an upper mounting portion, a lower mounting portion, an elastic training portion configured to provide a change in a resistance force on the upper mounting portion and the lower mounting portion when one of the upper mounting portion or the lower mounting portion is moved from a first position to a second position relative to the other mounting portion whereby the change in the resistance force affects the neuromuscular training of the body portion. In some embodiments, the upper mounting portion, the lower mounting portion and the elastic training portion are portions of an elastic training strap, the elastic training strap comprising at least one upper area of releasable attachment elements whereby the upper mounting portion of the elastic training strap is adapted to form an upper mounting facility and the elastic training strap comprising at least one lower area of releasable attachment elements whereby the lower mounting portion of the elastic training strap is adapted to form a lower mounting facility. In some embodiments, the resistance force is a progressive resistance force and in some embodiments, the resistance force is a configurable resistance force. In some embodiments, the resistance force is a progressive resistance force provided by the elastic training portion comprising a composite of tensile elements. In some embodiments, the composite of tensile elements comprises a first tensile element having a first tensile strength and a first resting length, a second tensile element having a second tensile strength greater than the first tensile strength and a second resting length longer than the first resting length whereby a first resistance force is provided through a first stretch range up to the second resting length and a second resistance force is provided in a second stretch range beyond the second resting length. In some embodiments, the upper mounting portion is configured to couple the elastic training portion to an upper mounting facility, the lower mounting portion is configure to couple the elastic training portion to a lower mounting facility and the elastic training strap portion is positioned between the upper mounting facility and the lower mounting facility.

One example embodiment of a training brace assembly comprises an upper mounting portion, a lower mounting portion, an elastic training portion coupled to the upper mounting portion and the lower mounting portion and the elastic training portion a adapted to provide a resistance force on the upper mounting portion and the lower mounting portion when one of the mounting portions is moved from a first position to a second position relative to the other mounting portion. In some embodiments, the resistance force is a progressive resistance force. In some embodiments, the upper mounting portion is a nonelastic upper mounting facility. In some embodiments, the resistance force is a progressive resistance force provided by the elastic training portion comprising a composite of tensile elements. In some embodiments the composite of tensile elements comprises, a first tensile element having a first tensile strength and a first resting length, a second tensile element having a second tensile strength greater than the first tensile strength and a second resting length longer than the first resting length whereby a first resistance force is provided through a first stretch range up to the second resting length and a second resistance force is provided in a second stretch range beyond the second resting length. In some embodiments, the training brace assembly further comprises an upper resistance point and a lower resistance point providing the resistance force on the upper mounting portion and the lower mounting portion. In some embodiments, the resistance force is a configurable resistance force provided by the elastic training portion being one from a group consisting of: the elastic training portion having one of a plurality of different lengths, the elastic training portion having one of a plurality of different composites of tensile elements, the elastic training portion comprising one of a plurality of elastic materials having different tensile properties, the elastic training portion comprising an adjustable length of the elastic training portion, and a first end of the elastic training portion having one of a plurality of attachment points on the lower mounting portion defining a lower resistance point and positioning a second end of the elastic training portion on one of a plurality of attachment points on the upper mounting portion defining an upper resistance point. In some embodiments, the resistance force has at least two magnitudes and at least two directions and the resistance force is configured to affect a desired training movement angle of a body portion when the training brace assembly is donned on the body portion. In some embodiments, the resistance force is configured to at least affect an abduction of a body portion when the training brace assembly is donned on the body portion. In some embodiments, a change in the resistance force affects a neuromuscular training of a body portion when the training brace assembly is donned on the body portion. In some embodiments, the elastic training portion is an elastic training strap, the upper mounting portion is an upper mounting facility comprising a nonelastic material having an inwardly facing surface to resist slippage when donned, the lower mounting portion is a lower mounting facility comprising a nonelastic material having an inwardly facing surface to resist slippage when donned and an upper resistance point and a lower resistance point providing the resistance force on the upper mounting portion and the lower mounting portion and the upper resistance point and a lower resistance point comprise the points where the elastic training strap is coupled to the upper and lower mounting facilities. In some embodiments, the lower mounting portion is configured to be positionable on an upper leg of a hip joint, the elastic training portion is configured to cross from a lower resistance point to an upper resistance point in a direction at least anterior and lateral to the upper leg, the elastic training portion is configured to cross below a greater trochanter of a femur of the upper leg, the upper resistance point being posterior to and above the greater trochanter whereby the resistance force affects an abduction of the upper leg when put in flexion.

One example of a method of training a body portion of a wearer provides a method comprising providing an elastic training portion of a training brace assembly, positioning a lower mounting portion and an upper mounting portion about a joint comprising the body portion, positioning the elastic training strap portion to extend between a lower resistance point on the lower mounting portion and an upper resistance point on the upper mounting portion and moving one of the upper or lower resistance points relative to the other creating a change in a tensile force on the elastic training strap portion whereby the change in the tensile force affects a neuromuscular training of the body portion. In some embodiments, the upper mounting portion is an upper mounting facility, the lower mounting portion is a lower mounting facility and the elastic training strap portion is coupled to the upper mounting facility at the upper resistance point and coupled to the lower mounting facility at the lower resistance point. In some embodiments, the method further comprises positioning the lower mounting facility on a leg of a hip joint of the wearer, positioning the upper mounting facility above a greater trochanter of the upper leg of the wearer, positioning the upper resistance point posterior to and above the greater trochanter of the upper leg, coupling the elastic training portion from the lower resistance point to the upper resistance point and positioning the lower resistance point whereby the elastic training portion crosses from the lower resistance point to the upper resistance point in a direction at least lateral to the upper leg and below the greater trochanter of the upper leg whereby a resistance force affects an abduction of the upper when the leg is put in flexion. In some embodiments, the elastic training portion crosses from the lower resistance point to the upper resistance point in a direction at least anterior and lateral to the upper leg and below the greater trochanter of the upper leg.

Embodiments of the training brace assembly are able to accommodate different joints, different size wearer's of the assembly and different tension settings such as for athletes during competition.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 7A illustrates another example embodiment of an elastic training portion;

FIG. 7B illustrates another example embodiment of an elastic training portion;

DETAILED DESCRIPTION OF THE INVENTION

Although embodiments of the training brace assembly are described below for use with neuromuscular training for the upper leg of a human, it is understood that the methods and systems described can be used for similar medical situations where training about joints may be needed for any mammalian. Notwithstanding the specific example embodiments set forth below, all such variations and modifications that would be envisioned by one of ordinary skill in the art are intended to fall within the scope of this disclosure.

Figure 2:
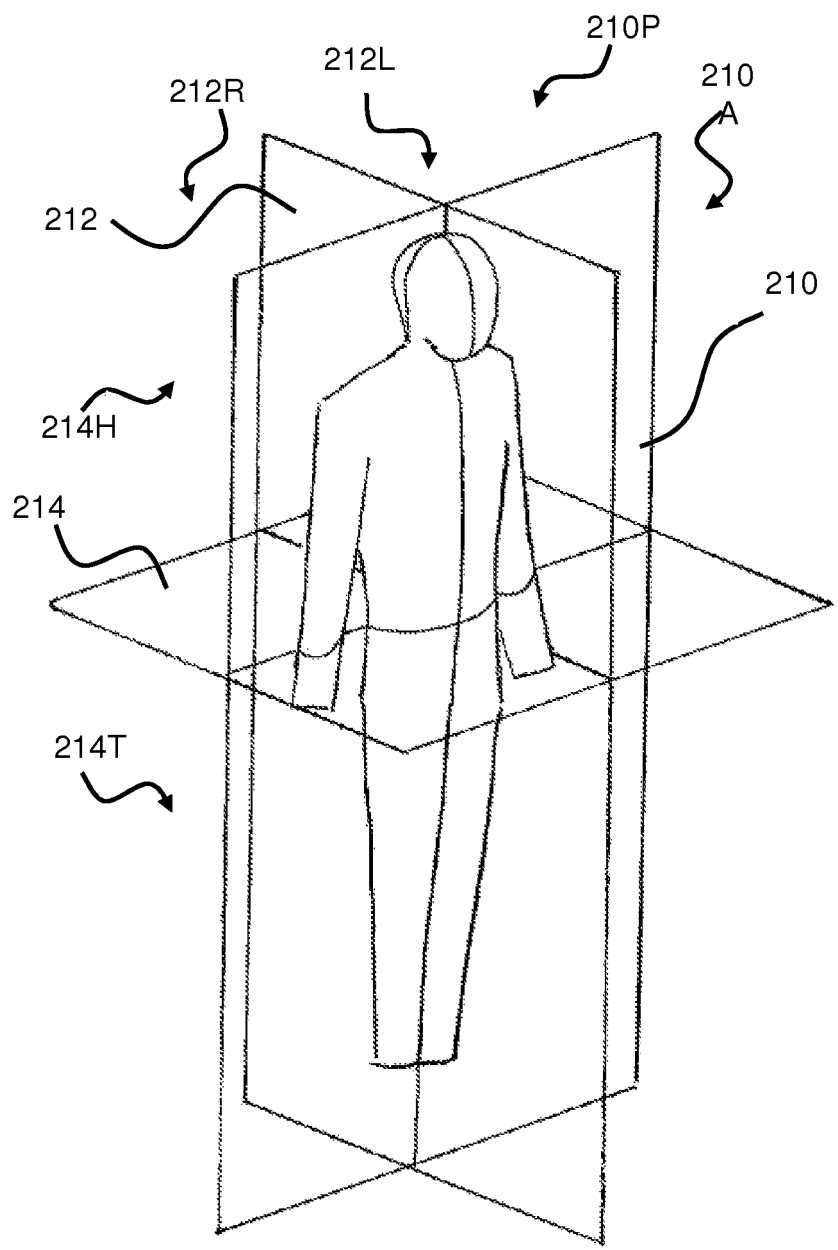
FIG. 2 provides an illustrative reference to the different anatomical planes used in this description.

As shown in FIG. 2, and as used throughout this description, the human body will be described as having three anatomical planes as shown, a midsagittal plane 212, a midcoronal plane 210 and a transverse plane 214. Midsagittal plane 212 is an imaginary vertical plane that divides the human body into a right portion or right lateral side 212R and a left portion or left lateral side 212L. Midcoronal plane 210 is an imaginary vertical plane that divides the body into an anterior or front side 210A and a posterior or rear side 210P. Transverse plane 214 is an imaginary horizontal plane that divides the body into a cranial or head portion 214H and a caudal or tail portion 214T that include a person's lower extremities.

Additionally, throughout the detailed description, the following terms and definitions will be used to describe joint movement and direction of movements with respect to the body:

Adduction: medial movement towards the midline of the body, such as moving an elbow and arm toward the side of the body;

Abduction: lateral movement away from the midline of the body such as moving the elbow and arm up and away from the side of the body or moving the upper leg up and away from the midline of the body;

Internal rotation: rotational movement about a longitudinal axis of a bone, the movement being an anterior portion of the body part rotates towards the center of the body such as turning an upper arm inward;

External rotation: rotational movement about a longitudinal axis of a bone, the movement being such that an anterior portion of the body part rotates away from the center of the body such as turning an upper arm outward;

Flexion: a decrease in the angle of a joint such as moving the hand towards the shoulder to flex the elbow or lifting the upper leg towards the chest to flex the hip; and Extension: an increase in the angle of the joint, for example moving the hand away from the shoulder extends the elbow.

Embodiments of this training brace assembly comprise a brace utilizing an elastic training portion to provide a variable resisting force to urge specific movement of a limb and/or urge specific movement of a muscle or muscle group. Typically, the variable resisting force is a progressive resisting force. And in some embodiments, the progressive resisting force includes a limiting force. The progressive resisting force exerts progressively greater resistance to an extension of a part of the training brace assembly brace as progressively greater force is applied to move or extend brace elements such as the mounting portions from each other. The progressive resistance thus acts against the forces extending the brace. In some embodiments, the progressive resistance included a limiting force that limits the movement of a portion of the brace by attempting to provide a resistance force equal to the forces extending the brace.

Embodiments of this training brace assembly may optionally include a flexible sleeve or other traditional brace components such as cuffs or mounts, or they may be integrated into undergarments or other clothing of the wearer. The elastic training portion and its position on the body helps hold the limb out of vulnerable positions and the muscles that are agonists do the same. When the wearer tries to put the limb in the bad position the muscles will learn to resist along with the elastic training portion. In some embodiments, the initial point of resistance may be provided mostly by the muscles and resistance can be provided by the elastic training portion near the end of the resistance or at its limiting point.

The configuration and application of restriction and urging forces from the training brace assembly through the movement of the joint may provide neuromuscular and proprioception training that lend strength and control to the movement by improving the body's ability to maintain stability with increased control of the muscles. Feedback from receptors in the joint, ligaments, tendons, and muscles train motor unit synchronization.

The training brace assembly and methods of the present invention address neuromuscular demands which form and control strength and positioning of specific muscles through different portions of a movement or motion. The training brace assembly and methods may impose proprioceptive demands that help train the central nervous system to store repeated patterns, thereby increasing the body's ability to perform proper movement about a joint. The training brace assembly and methods disclosed strengthen the muscles that prevent an undesired motion and they teach proper joint position and enhance proprioception. They will also be used to help reduce re-injury on return to activity.

One Embodiment of the Training Brace Assembly:

Although it is contemplated that embodiments of the training brace assembly can support many different types of skeletal joints such as elbows, shoulders, wrists, ankles, hips or knees, the illustrations and descriptions below will use an example embodiment directed to train the movement of a person's leg about a hip joint. Therefore, references to anatomical portions of the wearer's leg and hip are for illustration purposes and not as a limitation.

In one example embodiment of this training brace assembly, the training brace assembly comprises at least one elastic training portion, at least one upper mounting portion and at least one lower mounting portion. Generally, the elastic training portion is configured to provide a change in a resistance force on the upper and the lower mounting portions when one of the mounting portions is moved from a first position to a second position relative to the other mounting portion whereby the change in resistance force affects the neuromuscular training of the body portion. The resistance force is applied by the elastic training portion through upper and lower resistance points on the upper and lower mounting portions. Generally, the upper mounting portion is positioned and secured about one side of the limb or joint and the lower mounting portion is positioned and secured about the other side of the limb or joint to provide neuromuscular training of that body portion. The mounting portions themselves, or a coupling the mounting portions to mounting facilities, may position the mounting portions on each side of the limb or joint.

In some embodiments, the resistance force can be translated into at least two magnitudes and at least two directions and the resistance force is configured to affect a desired training movement angle of a body portion when the training brace assembly is donned on the body portion.

In some embodiments, the resistance force is configured to at least affect an abduction of a body portion when the training brace assembly is donned on the body portion.

In some embodiments, the change in the resistance force affects the neuromuscular training of a body portion when the training brace assembly is donned on the body portion.

In some embodiments, the resistance force provided by the elastic training portion is a progressive resistance force.

In one example embodiment, the upper mounting portion positions and secures the brace assembly about the hip area of a user, the lower mounting portion positions and secures the brace assembly about the thigh area of the user's leg and the elastic training portion of the training brace attaches to the upper and lower mounting portions whereby the elastic training portion of the training assembly can provide tensile force resisting the extension of the user's leg when the elastic training portion is properly positioned and attached to the upper and lower mounting facilities. As configured here, the elastic training portion provides multi-directional resistance to the extension of the user's leg such that it urges abduction and/or external rotation of the thigh, or the longitudinal axis of the femur, of the wearer.

In one embodiment of the training brace assembly, the upper mounting portion, the lower mounting portion and the elastic training portion are portions of an elastic training strap. In this embodiment, the elastic training strap has at least one upper area of releasable attachment elements whereby the upper mounting portion of the elastic training strap is adapted to form an upper mounting facility and the elastic training strap comprising at least one lower area of releasable attachment elements whereby the lower mounting portion of the elastic training strap is adapted to form a lower mounting facility.

In embodiments, the elastic training portion may comprise an elastic training strap that may be entirely elastic or the elastic training portion can have an elastic training portion coupled to the upper and lower mounting portions that have different or no elastic properties. In some embodiments, the upper and lower mounting portions are separate elements cooperating with the elastic training portion of the training brace. In some embodiments, the upper and lower mounting portions are portions of a single integrated garment.

Figure 1A:
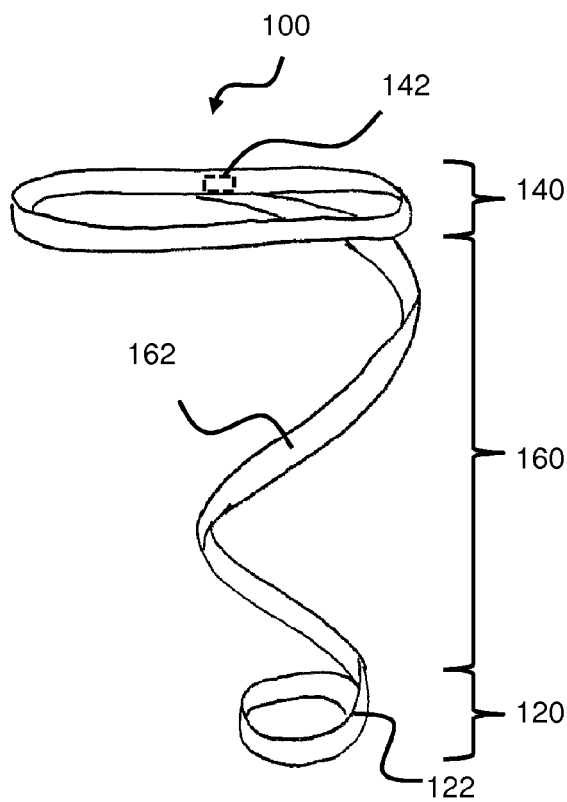
FIG. 1A illustrates a front view of one embodiment of the training brace assembly not mounted on a body portion.

In the example embodiment shown in FIG. 1A, the training brace assembly 100 is an elongated elastic training strap able to provide a progressive tensile resistance force. As shown, the training brace assembly 100 has a single continuous elastic training strap 162 configured to have an elastic training portion 160 an upper mounting portion 140 and a lower mounting portion 120. In this embodiment, where the assembly is a single elastic training strap 162, the lower mounting portion 120 wraps around the leg just above the knee forming a lower mounting facility and the upper mounting portion wraps around the waist forming an upper mounting facility. In these embodiments, the mounting facilities are frictionally secured to the body portion it is wrapped around. In this illustrative embodiment, since these facilities are secured to the body and connected to the elastic training portion 160, the points of connection between the elastic training strap portion and the mounting portions, here 142 an 122, define the resistance points. These resistance points provide the tensile force on the elastic training strap portion that forces the training of the limb. The attachment points can be provided by any attachment elements that couples the brace portions as described below. In this embodiment, the attachment point at 122 comprise a portion of releasable attachment elements on the inside surface of the elastic training portion 160 of the elastic training strap 162 that mates with a portion of releasable attachment elements on the outside surface of the lower mounting portion 120 and the attachment point at 142 comprises a portion of releasable attachment elements on the inside surface of the elastic training portion 160 of the elastic training strap 162 that mates with a portion of releasable attachment elements on the outside surface of the end of the upper mounting portion 140. In this embodiment, the attachment points and attachment elements also serve as the securing elements to secure the upper and lower mounting portions about their respective body portions.

FIG. B illustrates the embodiment of FIG. 1A on a wearer's hip and leg. In this example embodiment shown, the lower mounting portion is configured to be positionable on an upper leg of a hip joint, the elastic training strap portion 160 is configured to cross from the lower resistance point 122 to the upper resistance point in a direction at least anterior and lateral to the upper leg, the elastic training strap portion 160 is configured to cross below a greater trochanter 107 of a femur of the upper leg 104 and the upper resistance point being posterior to and above the greater trochanter 107 whereby the resistance force affects an abduction of the upper leg 104 when put in flexion. When this embodiment is mounted on a wearer's leg 104, the elastic training portion 160 extends from the anterior femur at the knee 105, and wraps posterior laterally and then wraps anterior medially until the elastic training strap extends on the anterior thigh and then extends laterally to couple with the wearer's upper mounting portion 140 generally at the wearer's waist 106. With this positioning, when the user puts their upper leg 104 in flexion, the tensile force on the elastic training portion 160 helps urge abduction or external rotation of the thigh by putting at least a two dimensional force on the longitudinal axis of the limb.

The elastic training portion of the training brace assembly can be made from any material to provide resistance to stretching in at least one direction. In one embodiment, the elastic training portion of the training brace is a pliable elastic material that provides progressive resistance to stretching and as the material stretches, the resistance to stretching increases. As an example, the resistance properties of embodiments function similar to the resistance properties of a rubber band. In one embodiment, the elastic material is similar to elastic sports tape. In other embodiments, the elastic material can comprise a rubber material, a plastic material or a spring material that can provide resistance properties. It is also contemplated that the elastic portion may comprise a combination of elastic and nonelastic material that still provide the elastic properties required of the elastic portion. As an example, and not for limitation purposes, these combinations may comprise combinations or laminates include cloths, fabrics, threads, struts or other materials combined with an elastic material through sewing, adhesives, Velcro attachment or even simple adjacent placement to elastic materials. These combinations or laminates may comprise multiple materials that can increase the adherence of the training assembly to itself or other materials and may be comprise combined materials at particular and not all areas of the assembly. Combinations of elastomeric materials with varying resistance properties are also contemplated.

In some embodiments, the resistance force is a progressive resistance force provided by the elastic training portion comprising a composite of tensile elements.

In some embodiments, the resistance force is a configurable resistance force provided by the elastic training portion having one of a plurality of different lengths, the elastic training portion having one of a plurality of different composites of tensile elements, the elastic training portion comprising one of a plurality of elastic materials having different tensile properties, the elastic training portion comprising an adjustable length of the elastic training portion and a first end of the elastic training portion having one of a plurality of attachment points on the lower mounting portion defining a lower resistance point and positioning a second end of the elastic training portion on one of a plurality of attachment points on the upper mounting portion defining an upper resistance point.

In some embodiments, the elastic training portion of the training brace assembly has a limiting resistance capability. For these embodiments, the limiting resistance may be provided by the elastic properties of the elastic portion reaching its maximum extension and therefore the portion provides a direct resisting force to further extension. This limiting resistance may also be provided by having a nonelastic material used in combination with an elastic material whereby when the limiting resistance point is met, the nonelastic material is engaged and that provides a preconfigured direct resisting force to any further extension of the elastic portion.

Figure 3A:
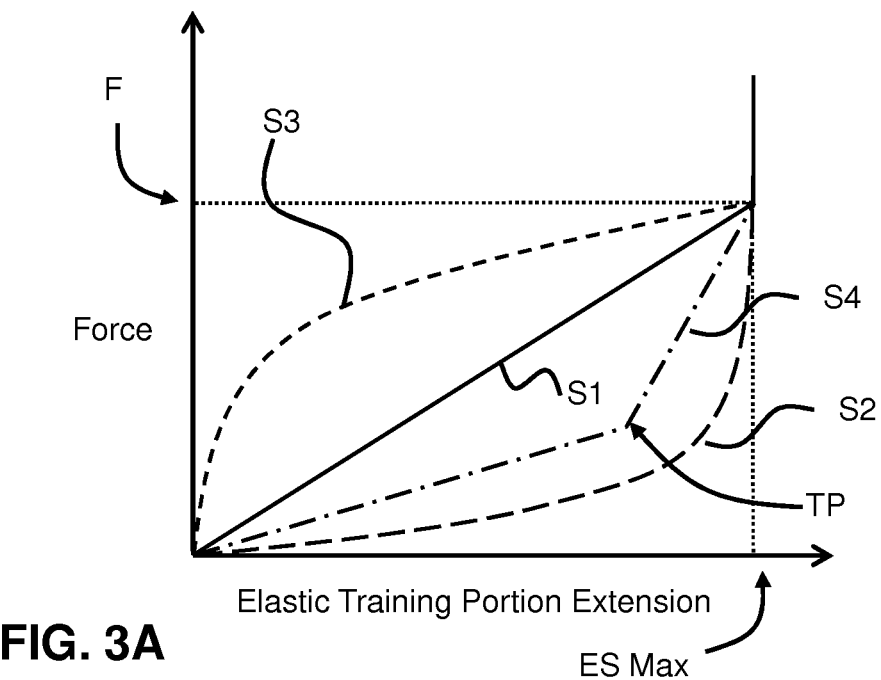
FIG. 3A graphically illustrates the tensile forces of multiple embodiments of an elastic training strap as a function of the strap extension.

To help illustrate the resistance properties of some elastic training straps functioning as the elastic training portion, FIG. 3A illustrates the resistance force that may be applied by the elastic training strap through a range of extensions of the elastic training portion. The Force axis represents the Resistance Force being provided by the elastic training portion from of force of zero (0) at a position where the elastic training portion is not extended to a force of F which represents the limiting resistance capability of the elastic training strap where the resistance force applied generally equals the extension force being applied. The Elastic Training Portion Extension axis represents the extension of the elastic training strap from an at rest position to a maximum extension position (ES Max). Line S1 represents a generally linear progressive resistance force to the extension that reaches its limiting resistance at maximum extension, ES Max. S2 represents a resistance force where the force gets increasingly stronger as ES Max is approached. For S2, when ES Max is reached, the resistance force equals the extension force. S3 represents a elastic training strap applying a resistance force that is progressively stronger, but increasing at a slower rate until the limiting force is met. Line S4 illustrates a resistance force that reflects a resistance being provided by the tensile properties of one material of one tensile element up to an extension point at which the resistance properties change at a transition point TP and from that extension point forward, the resistance being provided is from the tensile properties of a second tensile element. This profile of resistance force may be provided by an elastic training portion that comprises a composite of tensile elements as described later. For these example resistance profiles, when ES Max is reached, the limiting resistance of the elastic training strap equals the force applied.

Figure 3B:
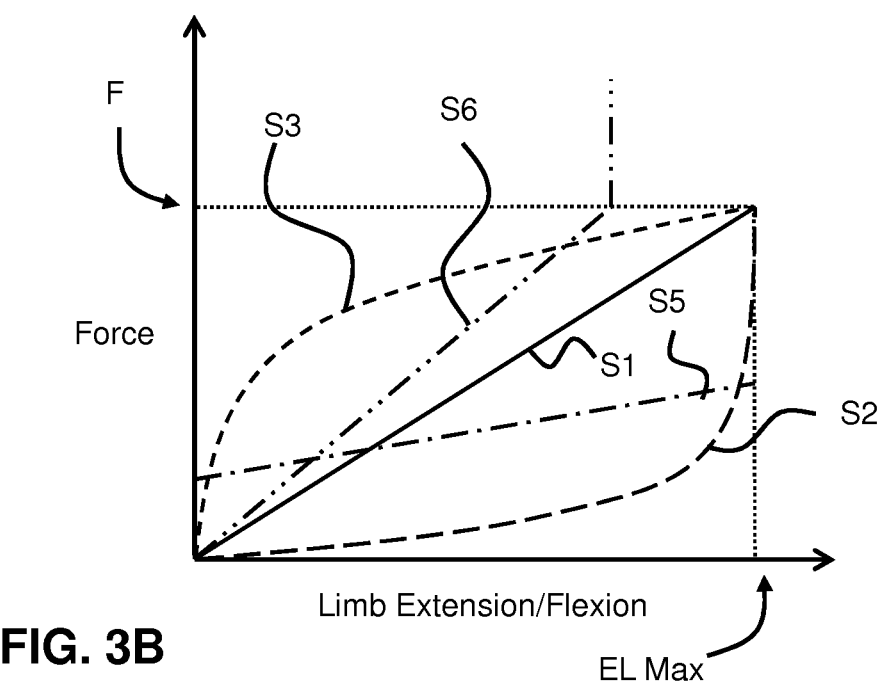
FIG. 3B graphically illustrates the tensile forces of multiple embodiments of an elastic training strap as a function of a limb extension/flexion.

FIG. 3B, illustrates the resistance force that may be applied by the elastic training strap through a range of extensions of the limb onto which the elastic training strap is mounted. Similar to FIG. 3A, lines S1, S2 and S3 represent resistance profiles where Limb Extension/Flexion is consistent with the Elastic Training Portion Extension. As shown with S5, some configurations of the elastic training portion may not provide a limiting force but the force may be limited by the limb extension or flexion. S5 also shows a "pre-tensioned" force applied to a limb that is not extended/flexed. Additionally, S6 illustrates a configuration where the limiting force of the elastic portion (ES Max of FIG. 3A) may be met prior to limb extension/flexion maximum (EL Max). The pre-tensioned and non-limiting configurations may be used with any configuration of elastic training portions.

The length, width and elastic properties of the elastic training portion of the training brace assembly can be varied based on the properties desired for the wearer and/or the sport the wearer will participate in. Different compounds provide different resistance tensions. One embodiment of the elastic training portion is made using Type II Silicone. The elastic training portion may also be made of liquid injection molded silicone and/or compression molded silicone. The material and process to manufacture the elastic training portion could vary depending on whether the elastic training portion is being custom made or whether it is mass produced. It is also contemplated that the materials such as rubber, styrene butadiene rubber, ethylene propylene rubber or latex may be used as materials for the elastic training portion.

FIG. 7A illustrates an example embodiment of an elastic training portion having a configuration that has variable elastic properties. In this design, the elastic training portion may have through holes 764 to reduce a cross-sectional profile of the elastic training strap providing the resistance. By reducing the cross-sectional profile, the area of strap providing resistance is reduced and the tensile strength of the strap is reduced. For example, a section having fewer through holes, such as the portion R1, may provide more tension that a section having more through holes such as R2 and R3. Additionally, holes could be offset either side of a centerline of the elastic training strap, or placed in a structured curve or any multiple number of configurations in order to provide accurate range of motion resistance and comfort.

In other embodiments, the elastic training portion of the training brace assembly has adjustment elements, such as buckles, that allow the elastic training strap to be adjusted to fit the wearer and provide different resistance properties.

Figure 8A:
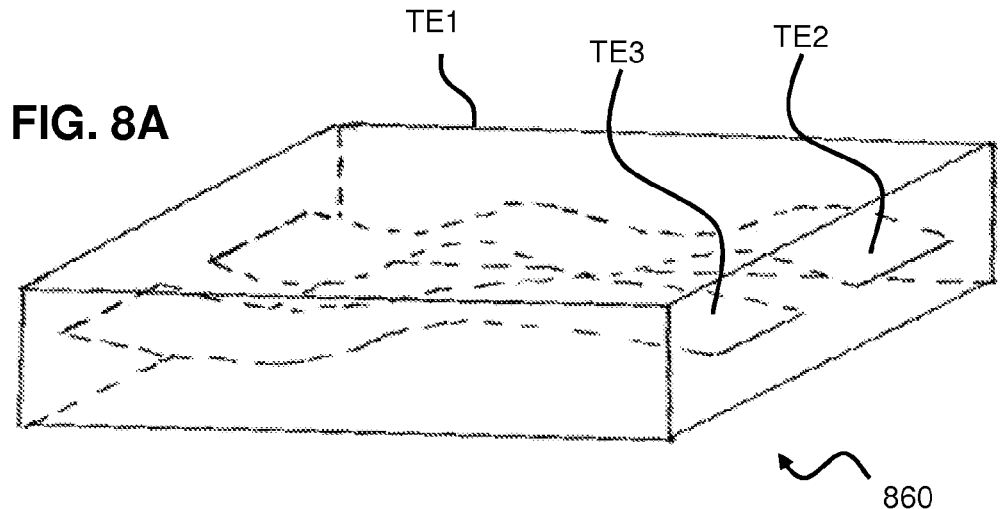
FIGS. 8A-8C illustrates various view of another example embodiment of an elastic training portion comprising a composite of elastic elements.
Figure 8B:
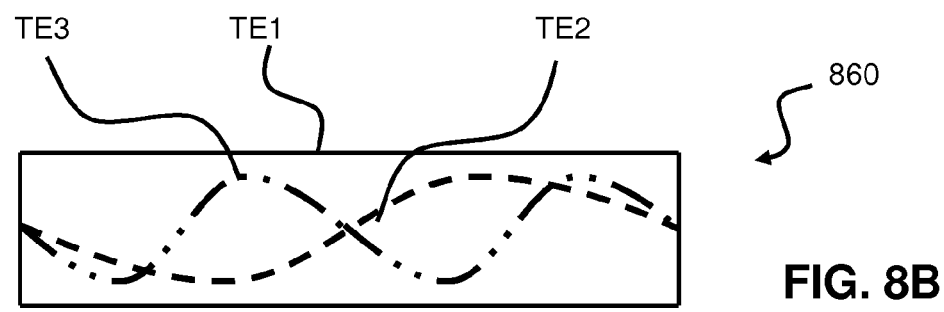

Although some of the discussion relates to a single elastic training portion of a training brace assembly, or a single elastic training strap, it is understood that multiple elastic training portions or elastic training straps can be used to provide the functional properties of the elastic training portion. More than one elastic training portion of the training brace assembly or elastic training strap can be used such that their properties combine to provide the desired resistance properties through the range of elastic training portions and limb extension. FIG. 8A shows a short section of a larger elastic training portion illustrating an example embodiment of a composite of tensile elements that combine to provide progressive tensile properties through the range of elastic training portion extension. This embodiment comprises a first tensile element TE1 having a first tensile strength and a first resting length, a second tensile element TE2 having a second tensile strength greater than the first tensile strength and a first resting length longer than the first resting length whereby a first resistance force is provided through a first stretch range up to the second resting length and a second resistance force is provided in a second stretch range beyond the second resting length. Although not required, in this embodiment, the second tensile element TE2 is molded within the first tensile element TE1. The elements may be molded by contracting the ends of the second tensile element TE2 so that a configured length coincides with the resting length of the first tensile element TE1 by creating evenly spaced waves along its length. The first tensile element TE1 may then be molded around the second tensile element TE2. Also illustrated is a third tensile element that may be used to provide a third resistance force at more than two ranges in the extension of the elastic training portion. FIG. 8B illustrates a side view of the section shown in FIG. 8A.

Figure 8C:

FIG. 8C illustrates the resting lengths of the first tensile element TE1, the second tensile element TE2 and the third tensile element TE3 before they are compacted to their configured lengths which in this embodiment coincide with the resting length of the first tensile element TE1. As shown, the second tensile element TE2 has a resting length, not tensioned or contracted, that is longer than the first tensile element TE1. The second tensile element TE2 is compressed so that a series of wavelengths shorten it to a configured length so that it is equal to the resting length of the first tensile element. The difference between the tensile element's resting length and its installed length defines at what point in an extension of the elastic training portion the second tensile element will transition (at a transition point) to start to provide significant resistance to further extension. Also shown are extension ranges where the different tensile elements will provide the primary resistance force. The first extension range ER1 illustrates the range of extension of the first tensile element TE1 and the second extension range ER2 illustrates the range of extension of the composite elastic training portion where the second tensile element TE2 will add to the resistance force. The third tensile element TE3 may add to the resistance force as the elastic training portion extends beyond the second extension range ER2. As can be seen through these example illustrations, the progressive resistance can be provided by selecting tensile elements with progressively higher resistance properties, defining resting lights for these tensile elements to coincide with a transition point where the elastic training portion should transition from one resistance force to another, and contracting each of the elements in a manner so that they have configured lengths that allow them to provide different resistance forces as the elastic training portion extends. In this embodiment, the configured length of the first tensile element TE1 is its resting length, the configured length of the second tensile element TE2 and the configured length of the third tensile element TE3 is the resting length of the first tensile element TE1.

Figure 8D:
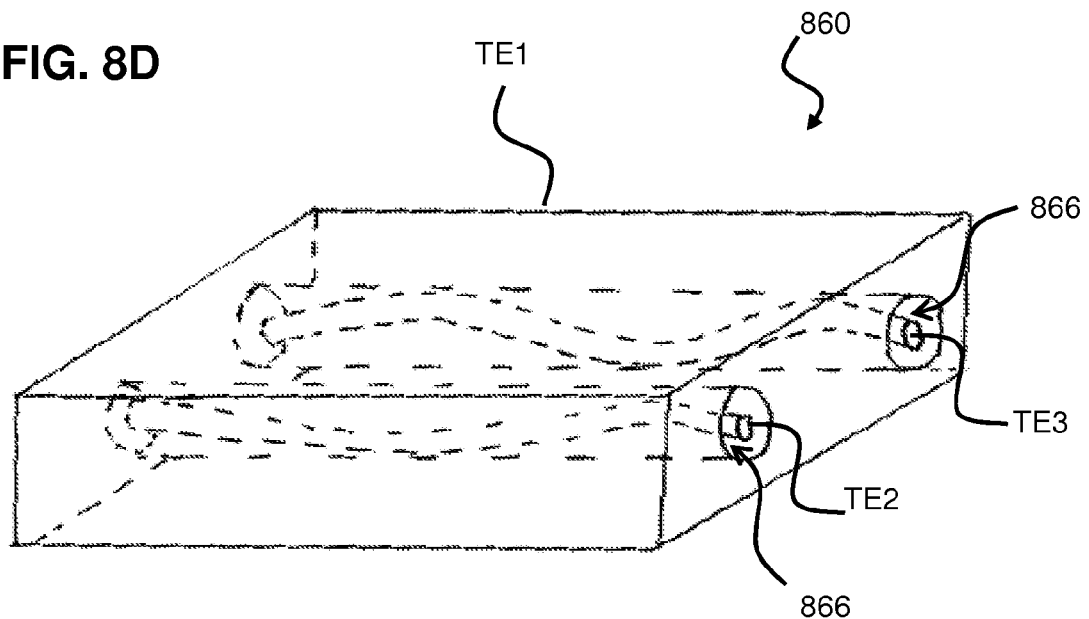
FIGS. 8D-8F illustrate various views of another example embodiment of an elastic training portion comprising a composite of elastic elements.
Figure 8E:
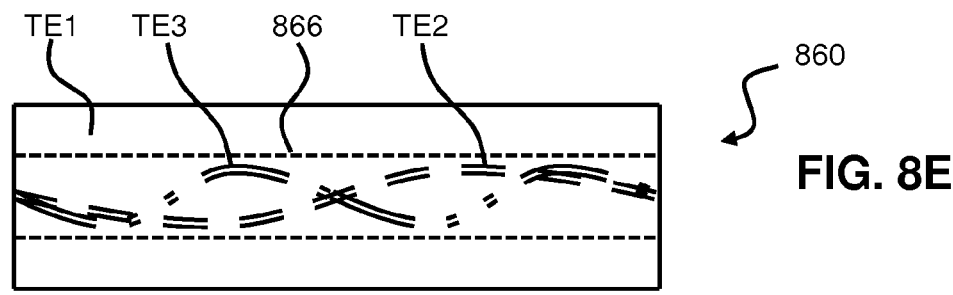
Figure 8F:
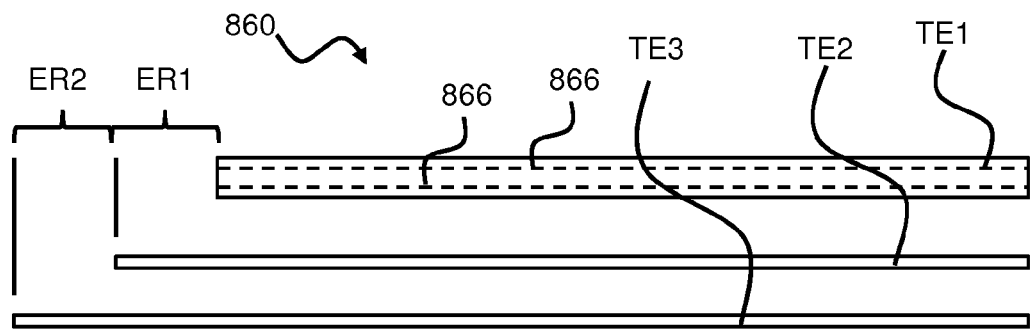

Is it also contemplated that other embodiments may include multiple tensile elements that are not embedded in each other but may be interwoven, independent or otherwise configured to provide the same type of progressive resistance properties as the elastic training portion extends. FIG. 8D-8F illustrate another embodiment of an elastic training portion comprising a composite of multiple tensile elements. In this example embodiment, the first tensile element TE1 has one or more channels 866 extending along its length. In these channels 866 are the second tensile element TE2 and the third tensile element TE3. Similar to the embodiment of FIGS. 8A-8C, as shown in FIG. 8F, each of the tensile elements have a resting length and a configured length that when the elastic training portion is extended, it transitions through different resistance forces. Each of the tensile elements may be secured in their configured length by any type of coupling elements that are capable of maintaining the tensile elements in position as the elastic training portion is subjected to tensile forces. These coupling elements may be connectors, clips or adhesives and may be placed at the ends of the tensile elements or at other locations of the elastic training portion.

FIG. 7B illustrates an example embodiment of an elastic training portion having multiple tensile elements TE1, TE2 and TE3.

Although not necessary, the elastic training portion of the training brace assembly may also contain regions having a frictional component or inwardly facing frictional surface on a portion of the assembly to resist slippage when worn by the wearer. These frictional components may be configured to frictionally engage with the limb, such at with the skin or garments of the wearer so that the frictional components help train the limb. For example, by combining different tensile properties in different portions of the elastic training portion with frictional properties of different portions of the elastic training portion on the skin or frictionally engaged garments on the skin of the wearer, different tensile forces can be applied to different portions of the elastic training portion and different resistance forces can be applied to different training brace assembly elements. FIG. 7A can be used to illustrated an embodiment where different tensile properties may be combined with frictional properties of the elastic training portion. Using this embodiment as an example, the section corresponding to R1 may have a frictional undersurface that engages the leg of the wearer so that section R1 may act as an anchor for that section and sections R2 and R3 could provide different tensile properties between the anchor of R1 and their respective ends of the elastic training portion. For example, since section R2 has a smaller through hole profile than would section R3, section R2 (between attachment point 722 and section R1) should be able to provide more resistance than section R3 (between attachment point 742 and section R1).

Referring back to FIG. 1A, training brace assembly further comprises a lower mounting portion 120. In this embodiment, a lower mounting facility is formed by the lower mounting portion 120 of the elastic training strap 162 that wraps around the leg and frictionally secures the lower mounting portion 120 to the leg just above the knee. In a preferred embodiment, this frictional securing is done with the use of non-slick surfaces on the underside or inwardly facing surface (the side positioned towards the body) of the lower mounting portion 120. Frictional securing may also be provided by regions of frictional components that can frictionally engage with the limb, and help hold the mounting portions in place so that the forces of the elastic training portion 160 can train the limb. Frictional securing of the mounting portion may also be provided by non-slick surfaces including but not limited to, high friction surfaces such as rubber, felt, mesh, leather or any combination of these surfaces.

In other embodiments, the lower mounting portion 120 may further comprise securing elements, such as straps, to engage the wearer's lower limb as well as attachment points 122 to provide elements to couple and/or position the mounting portion to itself or other portions or elements of the assembly. To secure the mounting portion to the wearer, any securing element may be used such as but not limited to: rigid fasteners such as rivets, adhesives or sewing; slidable attachment points such as slots or channels, pivoting fasteners such as rivets or buttons; and removable fasteners such as hook and loop type Velcro, buttons, clips, loops, buckles, snaps or hooks. Other suitable elements to secure the mounting portion to wearer include but are not limited to a sleeve around the limb, clothing articles and straps with adjusting facilities such as buckles. In this embodiment, the attachment points are also at the securing elements because this is where the elastic training strap transitions from the mounting portion to the elastic training portion of the elastic training strap.

In some embodiments, the lower mounting portion is provided by a separate element from other portions of the training brace assembly. Other embodiments of the lower mounting portion include but are not limited to a pad, cuff, portions of a sleeve, portions of a garment or any other element capable of mounting the training brace assembly to the wearer's limb and coupling the mounting portion to the elastic training portion of the brace.

In some embodiments, the lower mounting portion comprises a knee cuff or pad that can comprise any non-rigid material that can engage the wearer's leg and attach this pad to other elements of the training brace assembly. Suitable materials for this pad include but are not limited to cloth, cotton, plastic, nylon, mesh, rubber, silicon, latex and leather. This pad may further include padding or may be heat pliable, molded or contoured to be more comfortable for the wearer.

Attachment elements to couple and/or position the elastic training portion of the training brace assembly to the mounting portions include, but are not limited to any attachment elements such as but not limited to: rigid fasteners such as rivets, adhesives or sewing; slidable attachment points such as slots or channels, pivoting fasteners such as rivets or buttons; and removable fasteners such as hook and loop type Velcro, buttons, clips, loops, buckles, snaps or hooks. It is contemplated that attachment elements, such as with Velcro straps or buckles, will provide an ability for the elastic training strap to be releasably coupled, tightened or loosened as desired for comfort, support or specific resistance reasons.

The wrapping of the elastic portion of the brace around the leg may also be done once or multiple times.

The upper mounting portion positions the brace assembly about the upper limb or body portion about a user's limb. Embodiments of this portion can similarly include those types possible for the lower mounting portion. In the embodiment shown in FIG. 1B for the left leg, the elastic training strap is configured as a continuous elastic training strap that has an upper mounting portion 140 that wraps around itself to create the upper mounting facility. In this embodiment, the upper mounting portion 140 of the elastic training strap can provide the functionality of a cuff in traditional braces by wrapping the continuous elastic training strap around the wearer's waist and using securing elements to secure the training brace assembly to the waist. Sections of the upper mounting portion 140 of the training brace assembly may also contain attachment elements defining an attachment point (see 142 of FIG. 1A) that allows the upper mounting portion to attach to itself and to attach to the elastic training portion in particular places. Examples of attachment elements can include all those possible for the lower mounting facility. In one embodiment, the attachment elements comprise releasably mating Velcro sections attached on the interior of an upper end of the elastic training strap portion and attached on an exterior surface section of the upper mounting portion. These sections are placed on the training brace assembly in one or multiple pre-determined locations that will allow proper positioning of the elements and help ensure the attachment can be maintained posterior to the hip and towards a rear portion of the mounting facility.

Similar to the lower mounting portion, the upper mounting portion may include operably connected securing elements to secure the facility onto the wearer's body and frictional securing may also be provided.

In some embodiments, the elastic training portion is coupled to a waist strap as the upper mounting portion and upper mounting facility. This coupling may be made by a rigid sewing onto the waist strap or any attachment element described earlier. In embodiments where the upper mounting facility comprises a waist strap, the waist strap can comprise any material that can engage the wearer's waist and attach this waist strap to other elements of the training brace assembly. Suitable materials for this waist strap include but are not limited to cloth, cotton, plastic, nylon, mesh, rubber, silicon, latex and leather. This waist strap may be elastic or nonelastic and may further include padding or may be heat pliable, molded or contoured to be more comfortable for the wearer.

It is contemplated that in some embodiments, rather than coupling the elastic training portion of the training brace assembly to the upper and lower mounting portion, securing straps can also provide the attachment elements for the mounting portions to the elastic training portion. For example, the securing strap may wrap all the way around the limb or body and have the attachment elements so that when the securing strap is secured to the mounting facilities, the elastic training strap portions are attached to the securing strap.

The elastic training portion of the training brace assembly is attached to the upper and lower mounting portions at upper and lower attachment points by upper and lower attachment elements. This attachment can be made using any attachment elements described herein that that will mate with the attachment elements on the mounting portions to secure the ends of the elastic training portion of the training brace assembly onto the mounting portions.

Figure 1B:
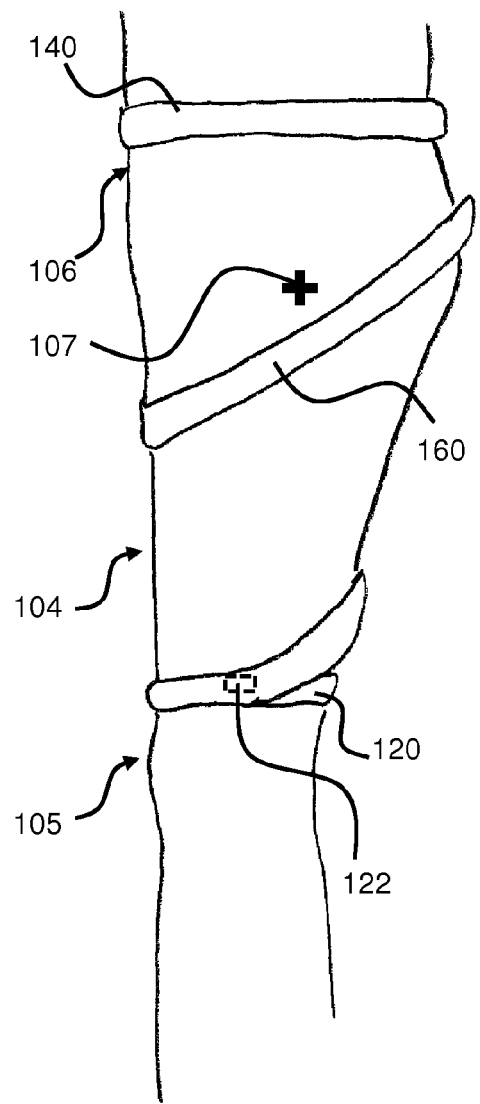
FIG. 1B illustrates a rear view of one embodiment of the training brace assembly mounted about the left hip and upper leg of a wearer.

In the embodiment of FIG. 1B, the elastic training portion 160 extends from the lateral femur 104, and wraps posterior medially and then wraps anterior laterally until the elastic training portion extends on the anterior thigh and then extends lateral and posterior medially to attach to the wearer's upper mounting portion 140 generally at the wearer's waist 106.

The configuration and location of the attachment points may be varied. In a preferred embodiment, the configuration of the attachment points are such that when the joint is moved in the direction to be trained, the elastic training portion of the training brace assembly is put into tension and the tensile force influences the abduction, adduction, flexion, extension and/or rotation of the limb. For training the upper leg of a human, the preferred configuration is with the force of the elastic training portion generally crossing at or below the rotational axis of the hip joint, or the greater trochanter. As shown in FIG. 1B, this is shown as the elastic portion 160 crossing beneath the greater trochanter 107.

For the embodiments shown in FIGS. 1A and 1B, the upper attachment point 142 functions generally as an upper resistance point the lower attachment point 122 functions as the lower resistance point. The resistance points represent the point on the training brace assembly where the tensile force of the elastic training portion will apply the resistance forces to the mounting portions.

The training brace assembly may also provide facilities that allow the resistance force to be a configurable resistance force. The resistance force may be configurable by including adjusting facilities that can be used to adjust the length or tension of the elastic training portion of the training brace assembly. By adjusting the length of the elastic training portion, the elastic tension and resistive properties of the training brace assembly can be adjusted. Adjustment elements may also comprise a buckle that allows the elastic training portion to be put through the buckle and adjusted. Examples of suitable adjusting facilities include but are not limited to providing buttons, Velcro, snaps or hooks or any type of adjustable connections or attachment elements that allow a connection that can alter the length or resistance properties of the elastic training strap. It is understood that providing elastic training straps of varying length is also another example of a suitable adjusting facility.

The training brace assembly may also provide a configurable resistance force by the elastic training portion having one of a plurality of different composites of tensile elements. Configurable resistance force may also be provided by the elastic training portion comprising one of a plurality of elastic materials having different tensile properties or a lower end of the elastic training portion having one of a plurality of attachment points on the lower mounting portion defining the lower resistance point and positioning an upper end of the elastic training portion on one of a plurality of attachment points on the upper mounting portion defining the upper resistance point.

In embodiments of this training brace assembly, it may be beneficial for the elastic training portion to provide a sufficient resistance force to the movement of a limb to force an adequate training of the limb. This resistance force is applied to the limbs about a joint by resisting movement of elements of the training brace itself in a certain direction and forcing the limb in a certain direction. By forcing or guiding the movement of the training brace assembly and limb, such as the external rotation and abduction of the femur as the knee rises, elements of the training brace assembly are able to help limbs move properly and resist improper movement as the limb moves.

Figure 5A:
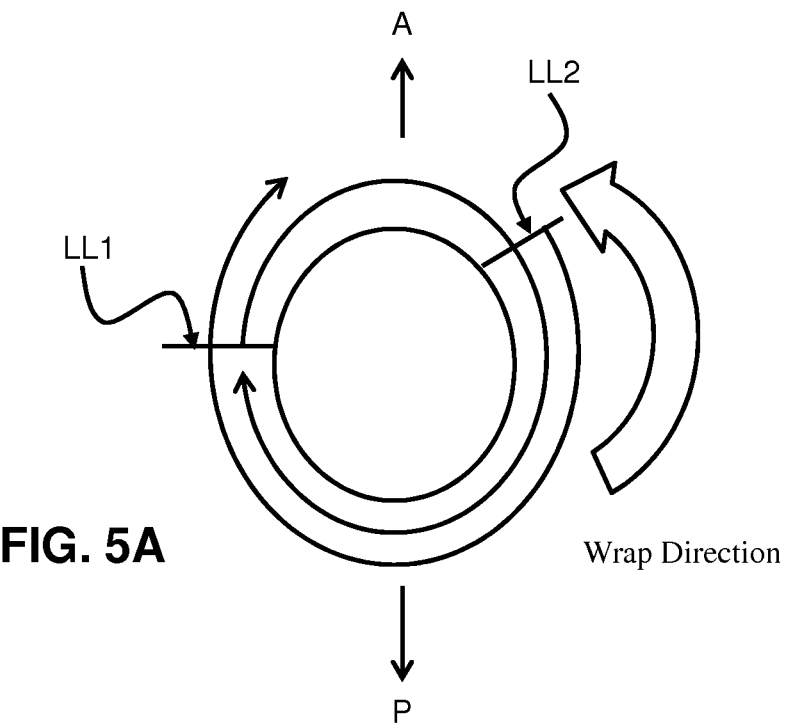
FIGS. 5A and 5B illustrates the wrap direction of some embodiments of the training strap and the general location of resistance points in relation to a wearer's leg and the wearer's hip.
Figure 5B:
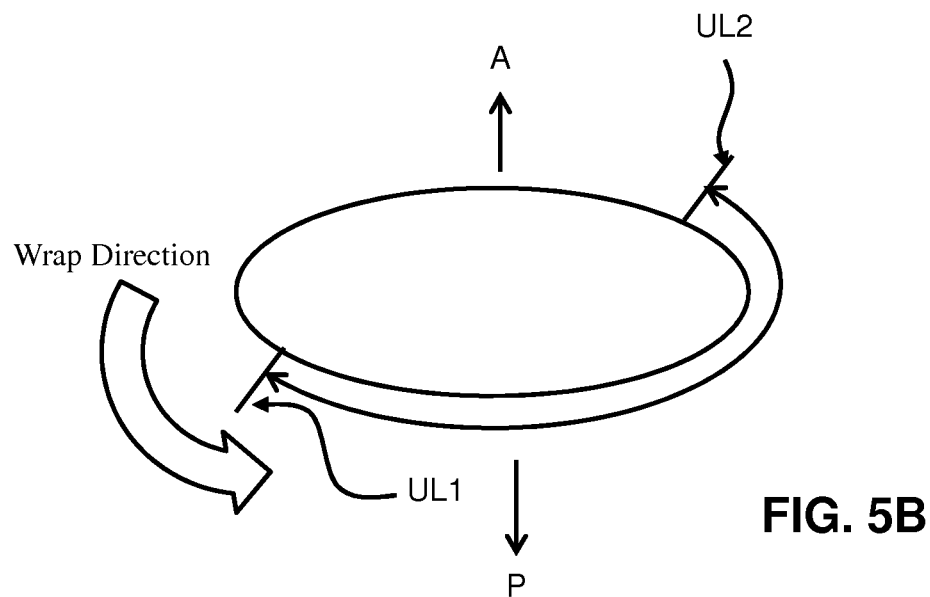

The directional force of the elastic training portion is provided by the directional placement of the mounting portions and elastic training portion on the limb. Specifically, the placement of the resistance points and the configuration of the elastic training portion between these points influence the force of the elastic training portion on the limb. FIGS. 5A and 5B illustrate example resistance point positioning for brace embodiments to train the left upper leg of a human with the training effect to be abduction and rotation of the leg as it moved in flexion. The arrows to "A" and "P" reflect the anterior and posterior direction in this view. Arrows also indicate the direction of wrapping for the elastic training portion in these views. FIG. 5A illustrates a top view of the lower mounting portion as it is mounted above the left knee of a wearer. The lower attachment point, as a lower resistance point, can be placed anywhere where the elastic training portion will provide some resistance at the lower resistance point when the leg is raised or put into flexion. In one embodiment, the positioning of the lower resistance point on the lower mounting portion is shown by the arrow starting from a lower limit 1 LL1 and extending to any point that allows the elastic strap portion to be wrapped beyond the lateral portion of the leg as shown. In one embodiment, a lower limit 2 LL2 between the anterior and medial portions of the leg defines another range of the lower resistance point extending back and then posterior to the leg, then lateral and anterior to the leg. The lower resistance point may be positioned by wrapping past the lateral portion one or multiple times. This placement reflects the elastic training portion being wrapped in the direction shown from the resistance point up to the upper mounting portion so that it at least crosses the lateral portion of the leg. FIG. 5B illustrates a top view of the upper mounting portion as it is mounted on a wearer's hip. The upper attachment point, as an upper resistance point, can be placed anywhere where the elastic training portion will provide some resistance when the leg is raised or put into flexion. In one embodiment, the range of the resistance point on the upper mounting portion is shown by the arrow between upper limit 1 UL1 and upper limit 2 UL2 so that the elastic training portion crosses at or below the rotational axis of the hip joint, or the greater trochanter. This placement reflects the elastic training portion wrapped from the direction shown from the resistance point on the lower mounting portion.

Other Embodiments of the Training Brace Assembly:

Another example embodiment of the training brace assembly comprises an elastic training portion, an upper mounting portion and a lower mounting portion, the elastic training portion coupled to the upper mounting portion and the lower mounting portion and the elastic training portion adapted to provide a resistance force on the upper mounting portion and the lower mounting portion when one of the mounting portions is moved from a first position to a second position relative to the other mounting portion.

Figure 9A:
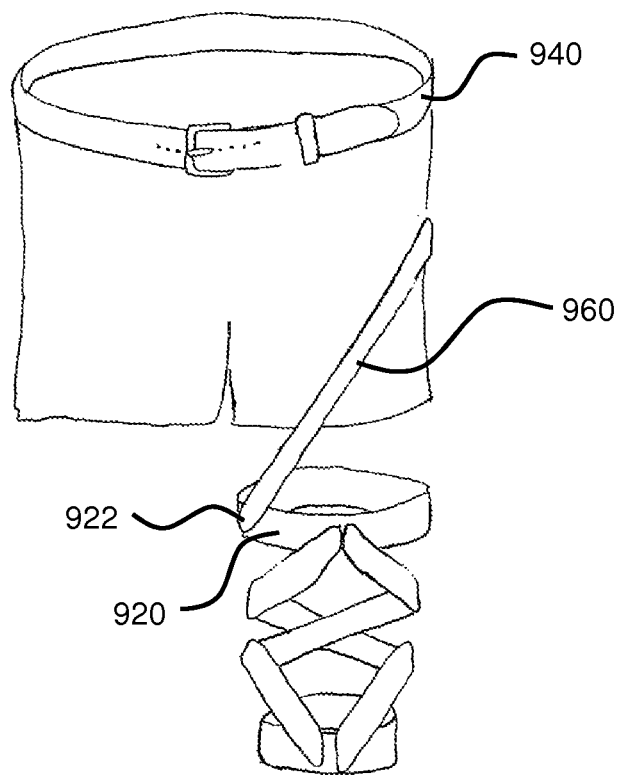
FIG. 9A illustrates a front view of another example embodiment of the training brace assembly.
Figure 9B:
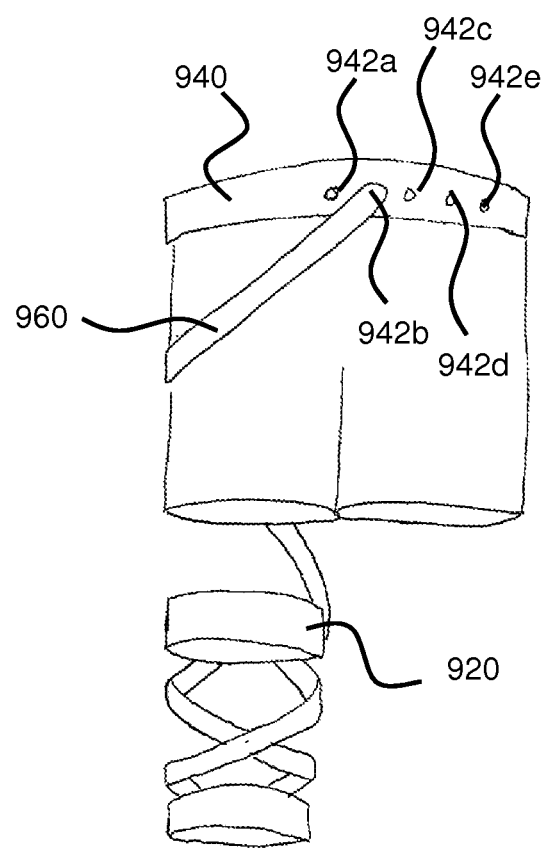
FIG. 9B illustrates a rear view of the example embodiment of FIG. 9A.

FIG. 9A illustrates a front view of another example embodiment and FIG. 9B shows a rear view of the same embodiment. As shown, the elastic training portion 960 may comprise an elastic training strap, the upper mounting portion 940 is an upper mounting facility, the lower mounting portion 920 is a lower mounting facility and the resistance points are the attachment points where the elastic training strap is coupled to the upper and lower mounting facilities. Both the upper mounting facility and the lower mounting facility may be made from a nonelastic material and may have an inwardly facing frictional surface to resist slippage of the facility when donned. The elastic training portion 960 may have any of the properties of the elastic training portions as described earlier. Although this example is shown with a garment under the upper mounting portion 940, this is optional. The upper mounting facility may be a separate pelvic belt or mounting facility such as a leather belt or plastic mount that would buckle or otherwise be frictionally secured near the wearer's waist. As shown, the lower mounting portion 920 may be a separate element such as a knee brace, here a cross-strap brace. The cross-strap brace may be those described in U.S. patent application Ser. No. 13/188,506 filed Jul. 22, 2011 and U.S. patent application Ser. No. 12/993,258, filed Nov. 18, 2010 both of which are incorporated herein by reference in their entirety. In this example embodiment, the upper mounting facility of the cross-strap brace functions as the lower mounting portion 920 of the training brace assembly. The embodiment in FIG. 9B also shows an example configuration of the training brace assembly having multiple attachment points 942a-942e on the upper mounting portion for adjusting the position of the elastic training portion. Additionally, the attachment point 922 of the elastic training portion 960 onto the lower mounting portion 920 may comprise multiple attachment points to provide some adjustment for the resistance force of the training brace assembly. The attachment points may be provided by mating attachment elements such as mating fasteners as described herein.

Figure 4A:
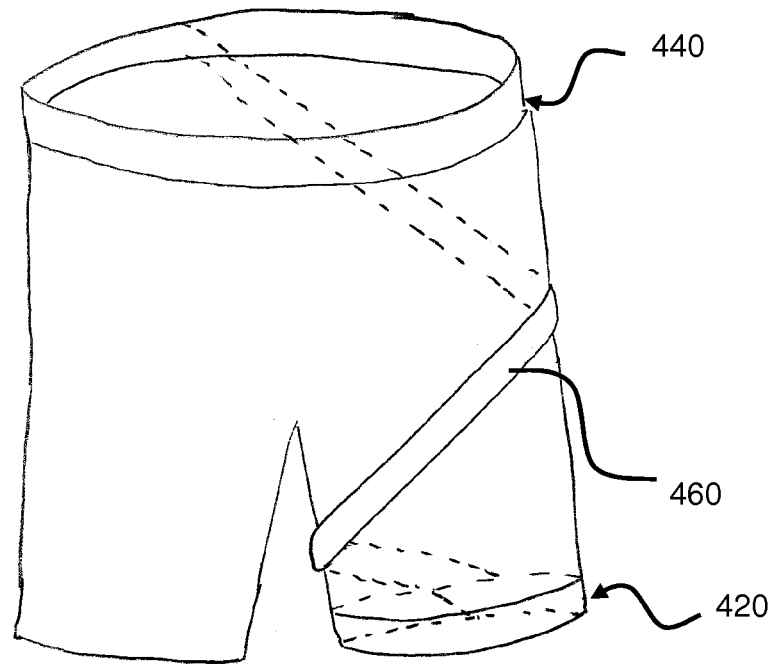
FIG. 4A illustrates a front view of one embodiment of the training brace assembly.
Figure 4B:
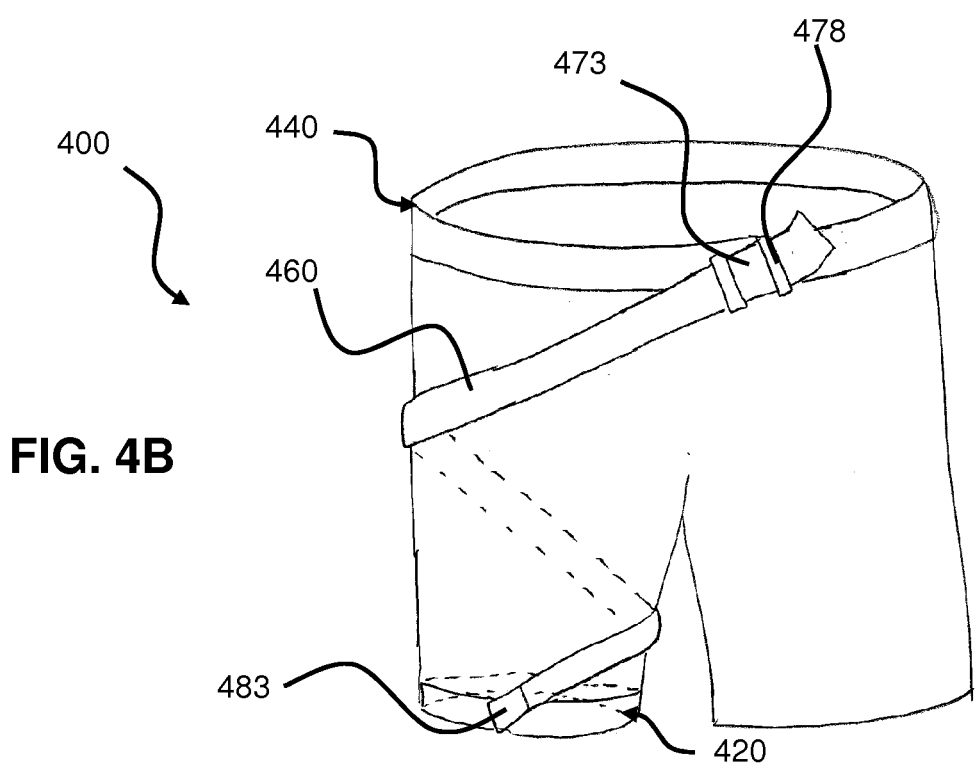
FIG. 4B illustrates a rear view of one embodiment of the training brace assembly.

Embodiments of a brace assembly may also include having a brace garment or sleeve to provide assembly elements. This type of embodiment is shown in FIGS. 4A and 4B where the upper and lower portions of the garment, 440 and 420 can function as the upper and lower mounting portions respectively and the elastic training portion 460 is coupled to these portions. The garment in these embodiments will rest against the wearer's skin. The surface of the garment that will touch the wearer's skin, the under sleeve, may be a non-slick surface to frictionally engage the wearers limb. It is contemplated that under sleeve material can be used so that the under garment is in contact with the skin around the knee to help keep the garment in place.

As shown in FIG. 4B, embodiments of the training brace assembly 400 can include mating fasteners as attachment elements at attachment points 473 and 483. These fasteners provide an attachment between the upper and lower mounting portions and the elastic training portion 460 and function as the attachment points. With this configuration, the attachment points (beneath strap fasteners) on the mounting portions mate with the fasteners 473 and 483. In this configuration, the placement of the fasteners 473 and 483 in different places of the training brace assembly adjusts the effective length of the elastic training portion about the wearer's body. This adjustment can be used in cooperation with the adjustment from the adjustment element 478, such as a buckle, to adjust the length of the elastic training strap.

Although not shown in FIG. 4A, embodiments of a garment based brace assembly may also have the elastic training portion of the training brace assembly connected directly to or integrated directly within the fabric of the garment.

Embodiments of the brace assembly can also be integrated with traditional brace elements such as upper or lower knee brace cuffs as well as structures for patellar control.

Figure 6A:
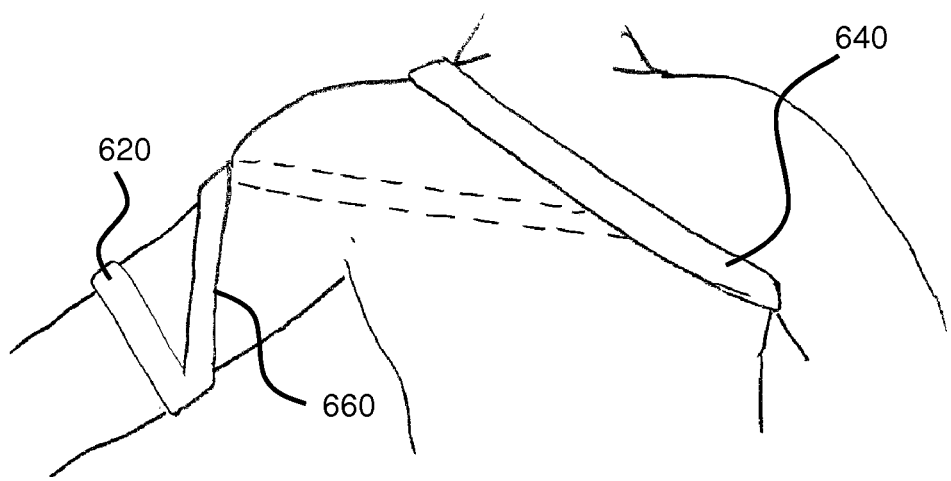
FIGS. 6A and 6B Illustrates some alternative embodiments of the training brace assembly.
Figure 6B:
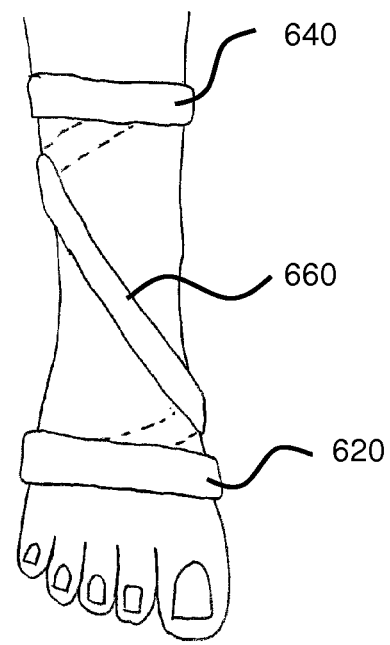

Although the above description and terminology of the components of the embodiments above utilize the terminology of a hip and leg, it is understood and contemplated that the assembly can be applied to other joints. For example, one embodiment of the assembly can be used with a person's shoulder joint or with an ankle. Example embodiments of the training brace assembly for other joints are shown in FIGS. 6A and 6B. These embodiments have an upper mounting portion 640, a lower mounting portion 620 and an elastic training portion 660 that generally are configured and used similar to the embodiments described for the hip joint. FIG. 6A illustrates one embodiment for use with a human upper arm that promotes a lateral rotation as the arm is lifted away from the body. FIG. 6B illustrates one embodiment for use with a human ankle. This embodiment promotes a lateral rotation of the foot as the ankle is put into extension.

One Embodiment of the Training Brace Assembly in Operation:

One embodiment of the disclosed inventions will be used to further illustrate the operational aspects of the invention. Although these illustrations utilize example embodiments about the hip of a wearer, it is understood that the training brace assembly may be used with other body portions such as a shoulder, ankle, knee, waist or elbow.

One example embodiment of a method of training a body portion of a wearer comprises providing a training brace assembly, positioning a lower mounting portion and an upper mounting portion about a joint, positioning the elastic training portion of the training brace assembly to extend between a lower resistance point on the lower mounting portion and an upper resistance point on the upper mounting portion and moving one of the upper or lower resistance points relative to the other creating a change in a tensile force on the elastic training portion whereby the change in tensile force creates a resistance force on the mounting portion that affects the neuromuscular training of the body portion. In one embodiment, the upper mounting portion is an upper mounting facility, the lower mounting portion is a lower mounting facility and the elastic training portion is coupled to the upper mounting facility at the upper resistance point and coupled to the lower mounting facility at the lower resistance point.

One example embodiment of the invention, as shown in FIGS. 1A and 1B, is used about a wearer's upper thigh 104 and hip 106. In this embodiment, the training brace assembly comprises an elastic training strap 162 having an elastic training portion 160, an upper mounting portion 140 and a lower mounting portion 120. The elastic training strap may be a continuous strap having the different portions or the strap may be a combination of portions coupled together to create the elastic training strap. As shown, the training brace assembly 100 is positioned with the lower mounting portion 120 just above the wearer's knee 105. This is done by positioning the lower mounting portion 120 on a leg 104 of a hip joint of the wearer, here above the knee 105 and wrapping the mounting portion 120 of the training brace assembly 100 around the leg 104 to secure the mounting portion 120. The mounting portions are secured to the body portions by securing elements that secure the mounting portions to themselves and the underside of the mounting portions then frictionally engages the body portion or engage garments frictionally engaging the body portion. A portion of the elastic training strap is also coupled to the lower mounting portion with attachment elements, such as matching Velcro fasteners to another portion of the elastic training strap, such that they create an attachment point 122. Once secured in place, from the attachment point 122, the elastic training portion 160 of the training brace assembly 100 is wrapped posterior and medial to the leg and continued anterior and lateral around the leg and posterior and medial until it is positioned at waist height and posterior to the wearer. Then, the upper mounting portion 140 of the training brace assembly 100 is wrapped around the waist 106 to secure the brace to the wearer's waist. Securing elements as described herein, such as Velcro, on the elastic training strap are secured to each other forming an upper mounting facility. Portions of the elastic training portion is also coupled to the upper mounting portion with attachment elements, such as matching Velcro fasteners on the elastic training portion, such that they create an attachment point 142 posterior on the waist. As with the lower mounting portion 120, the placement of the upper mounting portion 140 is done to minimize the movement of the facility.

Once this example embodiment is secured on the waist 106 and the thigh 104, such that the presence of the elastic training portion 160 of the training brace assembly helps urge the leg to rotate and abduct when the leg is lifted and put into flexion. The elastic properties of the elastic training portion 160 of the training brace assembly can provide resistive properties early in the motion arch of the joint thereby help train early in the motion arch. As the leg is lifted towards the chest, the elastic training portion stretches and may provide progressively more resistance as the leg is lifted. When the leg reaches a desired limit, the elastic training portion reach a significant resistance level, which may be a limiting resistance force, that prevents further extension. This resistance may or may not be a hard stop of the movement. This resistance approach uniquely provides therapeutic benefits such as increasing neuromuscular control and causing the extensor and flexor muscles to gradually strengthen which is beneficial for joint stability. For example, neuromuscular control of the hip abductor muscles can be increased with this example embodiment by configuring the elastic training portion training to train the proper movement of these muscles.

The point of attachment, attachment points 142 and 122, of the elastic training portions and the upper and lower mounting portions are such that the desired resistance provided by the resistance points allow proper leg movement. Additionally, if the training brace assembly 100 has good frictional contact with the skin, rotational support of the knee joint is also provided. To further assist in providing knee support, the lower mounting facility may also be placed below the knee of the wearer. As the wearer uses the training brace assembly, and as their need for support and/or comfort changes, the elastic training portions can be tightened or loosened to change the elastic tension on the system by simply adjusting the elastic training portion with adjustment elements such as removing and reattaching the elastic training straps with Velcro hook and loop type fasteners, changing strap lengths with a buckle to changing to straps with different tensile properties.

The example embodiment of FIGS. 9A and 9B operates similar to those of FIGS. 1A and 1B. In this embodiment, the lower mounting facility 920 is positioned on the leg of a hip joint of the wearer, the upper mounting facility 940 is positioned above the greater trochanter of the upper leg of the wearer, the upper resistance point is positioned posterior to and above the greater trochanter of the upper leg, the elastic training portion 960 is coupled from the lower resistance point 922 to the upper resistance point 942b. The lower resistance point 922 is positioned whereby the elastic training portion 960 crosses from the lower resistance point 922 to the upper resistance point 942b in a direction at least anterior and lateral to the upper leg and below the greater trochanter of the upper leg whereby the resistance force affects an abduction of the upper when the leg is put in flexion.

The example embodiment of FIGS. 4A and 4B operates similar to those of FIGS. 1A and 1B. In this embodiment, the garment includes both the upper mounting portion 440 and the lower mounting portion 420. The elastic training portion 460 of the training brace assembly 400 is an elastic training strap. The elastic training strap 460 is initially attached to the lower mounting portion 420 and wrapped around the posterior of the leg medially and then anterior to the leg laterally and up to the posterior waist to be attached to the upper mounting portion 440. In this embodiment, the resistance points are at the attachment points 483 and 473 of the elastic training strap.

The embodiments of FIGS. 6A and 6B operate similar to the embodiments described for FIGS. 1A, 1B and 4 on different joints.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

I claim:

1. A training brace assembly comprising:
   an elastic training portion, an upper mounting portion and a lower mounting portion;
   the elastic training portion coupled to the upper mounting portion and the lower mounting portion;
   the elastic training portion configured to provide a resistance force on the upper mounting portion and the lower mounting portion when one of the mounting portions is moved from a first position to a second position relative to the other mounting portion wherein the resistance force is configured to at least affect an abduction of a body portion when the training brace assembly is donned on the body portion and the body portion is put in flexion;
   the lower mounting portion is configured to be positionable on an upper leg of a hip joint;
   the elastic training portion is configured to cross from a lower resistance point to an upper resistance point in a direction at least lateral to the upper leg;
   the elastic training portion is configured to cross below a greater trochanter of a femur of the upper leg; and
   the upper resistance point being posterior to and above the greater trochanter of the femur whereby the resistance force affects an abduction of the upper leg when the upper leg is put in flexion.

2. The training brace assembly of claim 1 wherein the resistance force is a progressive resistance force.

3. The training brace assembly of claim 1 wherein the upper mounting portion is a nonelastic upper mounting facility.

4. The training brace assembly of claim 1 wherein the upper resistance point provides the resistance force on the upper mounting portion and the lower resistance point provides the resistance force on the lower mounting portion.

5. The training brace assembly of claim 1 wherein the resistance force is a configurable resistance force provided by the elastic training portion being one from a group consisting of:
   the elastic training portion having one of a plurality of different lengths;
   the elastic training portion having one of a plurality of different tensile elements;
   the elastic training portion comprising one of a plurality of elastic materials having different tensile properties;
   the elastic training portion comprising an adjustable length of the elastic training portion; and
   a first end of the elastic training portion having one of a plurality of attachment points on the lower mounting portion defining the lower resistance point and positioning a second end of the elastic training portion on one of a plurality of attachment points on the upper mounting portion defining the upper resistance point.

6. The training brace assembly of claim 1 wherein a change in the resistance force affects a neuromuscular training of the body portion when the training brace assembly is donned on the body portion.

7. The training brace assembly of claim 1 wherein:
the elastic training portion is an elastic training strap;
the upper mounting portion is an upper mounting facility comprising a nonelastic material having an inwardly facing surface to resist slippage when donned;
the lower mounting portion is a lower mounting facility comprising a nonelastic material having an inwardly facing surface to resist slippage when donned;
the upper resistance point and the lower resistance point providing the resistance force on the upper mounting portion and the lower mounting portion; and
the upper resistance point and the lower resistance point comprise an upper attachment point and a lower attachment point where the elastic training strap is coupled to the upper and lower mounting facilities.

8. A training brace assembly for a body portion, the assembly comprising:
an upper mounting portion;
a lower mounting portion;
an elastic training portion;
the elastic training portion is configured to couple to the upper mounting portion at a position posterior to a joint of the body portion when the training brace assembly is donned about the joint of the body portion;
the elastic training portion is configured to provide a change in a resistance force on the upper mounting portion and the lower mounting portion when one of the upper mounting portion or the lower mounting portion is moved from a first position to a second position relative to the other mounting portion whereby the change in the resistance force affects the neuromuscular training of the body portion;
the resistance force is a progressive resistance force provided by the elastic training portion comprising a composite of tensile elements aligned generally parallel to each other; and
the composite of tensile elements comprises:
a first tensile element having a first tensile strength and a first resting length, and a second tensile element having a second tensile strength greater than the first tensile strength and a second resting length longer than the first resting length whereby a first resistance force is provided through a first stretch range up to the second resting length and a second resistance force is provided in a second stretch range beyond the second resting length.

9. The training brace assembly of claim 1 wherein:
the upper mounting portion, the lower mounting portion and the elastic training portion are portions of an elastic training strap;
the elastic training strap comprising at least one upper area of releasable attachment elements whereby the upper mounting portion of the elastic training strap is adapted to form an upper mounting facility; and
the elastic training strap comprising at least one lower area of releasable attachment elements whereby the lower mounting portion of the elastic training strap is adapted to form a lower mounting facility.

10. The training brace assembly of claim 1 wherein the joint of the body portion is one of a shoulder or an ankle.

11. The training brace assembly of claim 1 wherein:
the upper mounting portion is configured to couple the elastic training portion to an upper mounting facility;
the lower mounting portion is configure to couple the elastic training portion to a lower mounting facility; and
the elastic training portion is positioned between the upper mounting facility and the lower mounting facility.

12. A method of training a body portion of a wearer, the method comprising:
providing an elastic training strap portion of a training brace assembly;
positioning a lower mounting portion and an upper mounting portion about the body portion comprising a joint;
positioning the elastic training strap portion to extend between a lower resistance point on the lower mounting portion and an upper resistance point on the upper mounting portion;
extending the elastic training strap portion from a point medial to the joint in a direction anterior and lateral and posterior to the joint to the upper resistance point; and
moving one of the upper or lower resistance points relative to the other creating a change in a tensile force on the elastic training strap portion whereby the change in the tensile force affects a neuromuscular training of the body portion.

13. The method of claim 12 wherein:
the upper mounting portion is an upper mounting facility;
the lower mounting portion is a lower mounting facility; and
the elastic training strap portion is coupled to the upper mounting facility at the upper resistance point and coupled to the lower mounting facility at the lower resistance point.

14. The method of claim 13 further comprising:
positioning the lower mounting facility on a leg of a hip joint of the wearer;
positioning the upper mounting facility above a greater trochanter of the leg of the wearer;
positioning the upper resistance point posterior to and above the greater trochanter of the leg;
coupling the elastic training strap portion from the lower resistance point to the upper resistance point; and
positioning the lower resistance point whereby the elastic training strap portion crosses from the lower resistance point to the upper resistance point in a direction at least anterior and lateral and posterior to the leg and below the greater trochanter of the leg whereby a resistance force affects an abduction of the leg when the leg is put in flexion.

15. A training brace assembly comprising:
an elastic training portion, an upper mounting portion and a lower mounting portion;
the elastic training portion coupled to the upper mounting portion and the lower mounting portion;
the elastic training portion adapted to provide a resistance force on the upper mounting portion and the lower mounting portion when one of the mounting portions is moved from a first position to a second position relative to the other mounting portion wherein the resistance force is configured to at least affect an abduction of a body portion when the training brace assembly is donned on the body portion and the body portion is put in flexion; and
the resistance force has at least two magnitudes and at least two directions about a longitudinal axis of a body portion and the resistance force is configured to affect a desired training movement angle of the body portion when the training brace assembly is donned on the body portion.

16. The training brace assembly of claim 15 wherein the resistance force is a progressive resistance force.

17. The training brace assembly of claim 15 wherein the body portion is an upper leg of a hip.

18. A training brace assembly comprising:
    an elastic training portion, an upper mounting portion and a lower mounting portion;
    the elastic training portion coupled to the upper mounting portion and the lower mounting portion;
    the elastic training portion adapted to provide a resistance force on the upper mounting portion and the lower mounting portion when one of the mounting portions is moved from a first position to a second position relative to the other mounting portion wherein the resistance force is configured to at least affect an abduction of a body portion when the training brace assembly is donned on the body portion and the body portion is put in flexion;
    the resistance force is a progressive resistance force provided by the elastic training portion comprising a composite of tensile elements aligned generally parallel to each other;
    the composite of tensile elements comprises:
        a first tensile element having a first tensile strength and a first resting length; and
        a second tensile element having a second tensile strength greater than the first tensile strength and a second resting length longer than the first resting length whereby a first resistance force is provided through a first stretch range up to the second resting length and a second resistance force is provided in a second stretch range beyond the second resting length.

* * * * *